(12) United States Patent
Basset et al.

(10) Patent No.: US 6,878,660 B2
(45) Date of Patent: Apr. 12, 2005

(54) CATALYST FIXED ON A CARRIER AND USED FOR THE METATHESIS OF OLEFINS

(75) Inventors: Jean-Marie Basset, Caluire (FR); Mathieu Chabanas, Condrieu (FR); Christophe Coperet, Lyons (FR)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/363,858
(22) PCT Filed: Sep. 14, 2001
(86) PCT No.: PCT/EP01/10675

§ 371 (c)(1),
(2), (4) Date: Mar. 14, 2003

(87) PCT Pub. No.: WO02/22262

PCT Pub. Date: Mar. 21, 2002

(65) Prior Publication Data

US 2003/0181776 A1 Sep. 25, 2003

(30) Foreign Application Priority Data

Sep. 15, 2000 (DE) .......................................... 100 46 143

(51) Int. Cl.⁷ ................................................. B01J 31/00
(52) U.S. Cl. ........................ 502/150; 502/102; 502/152
(58) Field of Search ................................ 502/150, 152, 502/102

(56) References Cited

U.S. PATENT DOCUMENTS

| | | | |
|---|---|---|---|
| 4,818,442 A | | 4/1989 | Vanderveen et al. |
| 5,087,710 A | | 2/1992 | Schrock et al. |
| 5,146,033 A | | 9/1992 | Schrock et al. |
| 5,175,311 A | * | 12/1992 | Doyle ......................... 549/302 |
| 5,296,566 A | * | 3/1994 | Brown-Wensley et al. . 526/171 |
| 5,296,595 A | * | 3/1994 | Doyle ......................... 540/200 |
| 5,342,985 A | | 8/1994 | Herrmann et al. |
| 5,491,206 A | * | 2/1996 | Brown-Wensley et al. . 526/126 |
| 5,672,803 A | * | 9/1997 | Smith et al. ................. 585/646 |
| 5,905,055 A | * | 5/1999 | Verdonck et al. ............ 502/311 |
| 6,534,431 B1 | * | 3/2003 | Suntola et al. ................. 502/60 |
| 6,538,168 B1 | * | 3/2003 | Schwab et al. .............. 585/647 |

FOREIGN PATENT DOCUMENTS

| | | |
|---|---|---|
| FR | 2 525 224 | 10/1983 |
| WO | 98 02244 | 1/1998 |

OTHER PUBLICATIONS

W A Herrmann: "Essays on organometallic chemistry, VII. Laboratory curiosities of yesterday, catalysts of tomorrow: organometallic oxides" Journal of Organometallic Chemistry, vol. 500, No. 1, pp. 149–173, Sep. 1, 1995.

W.A. Herrmann et al.: "Methyltrioxorhenium as catalyst for olefin metathesis" Angewandte Chemie, vol. 30, No. 12, pp. 1636–1638 1991.

F. Schekler–Nahama et al.: "Influence of Lewis acidity of rhenium heptoxide supported on alumina catalyst on the catalytic performances in olefin metathesis" Applied Catalysis A: General, vol. 167, No. 2, pp. 237–245, Feb. 27, 1998.

Database CA [Online], Chemical Abstracts Service Database accession No. 118:124718 CA XP002191428.

Database CA [Online], Chemical Abstracts Service Database accession No. 112:158626 CA XP002191429.

K. Weiss et al.: "Heterogenous, metathesis–active Schrock–type carbine complexes by reaction of carbine tungsten(VI) complexes with silica gel" Angewandte Chemie, vol. 28, No. 1, pp. 62–64, 1989.

R. Buffon et al.: "Molecular heterogenous metathesis catalysts: an attempted synthesis of surface–anchored alkylidenetungsten complexes" Journal of the Chemical Society, pp. 1723–1729, 1994.

Anne M. LaPointe et al.: "Alkyl, alkylidene, and alkylidyne complexes of rhenium" Organometallics, vol. 14, No. 4, pp. 1875–1884, 1995.

Robert Toreki et al.: "Synthesis and characterization of rhenium(VIII) alkylidene alkylidyne complexes of the type Re(CR') (CHR') (OR)2 and related species" Journal of the Americal Chemical Society, vol. 114, No. 9, pp. 3367–3380, 1992.

A.D. Horton et al.: "Preparation of Bis and Tris(arylimido) complexes of Rhenium(VII), including Bis(arylimido) neopentylidene complexes, candidates as olefin metathesis catalysts" Polyhedron, vol. 7, No. 19/20, pp. 1841–1853, 1988.

Colin J. Schaverien et al: "A well–characterized, highly active, Lewis acid free olefin metathesis catalyst" J. Am. Chem. Soc., vol. 108, pp. 2771–2773, 1986.

* cited by examiner

Primary Examiner—Mark L. Bell
Assistant Examiner—Jennine M. Brown
(74) Attorney, Agent, or Firm—Oblon, Spivak, McClelland, Maier & Neustadt, P.C.

(57) ABSTRACT

The present invention relates to a novel, heterogeneous catalyst which is suitable, in particular, for olefin metathesis. This catalyst is immobilized on an inorganic support and contains at least one active rhenium compound containing at least one carbene group and, if desired, further functional groups. The rhenium compound is bonded to the material used as support by a chemical bond.

32 Claims, No Drawings

CATALYST FIXED ON A CARRIER AND USED FOR THE METATHESIS OF OLEFINS

The present invention relates to an olefin metathesis process in which rhenium/carbene complexes are used as catalysts which have relatively high activities due to specific immobilization on the surface of a suitable support.

The term olefin metathesis is taken to mean the reaction of two olefins with one another, with new olefins being formed by the breaking and re-formation of the olefinic double bond. This is shown in a simplified manner in the following scheme.

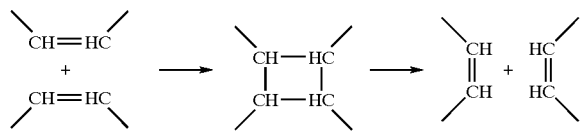

A distinction is made between various metathesis reactions. For the case of the metathesis of acyclic olefins, a distinction is furthermore made between self-metathesis, in which an olefin is turned into a mixture of two olefins of different molar mass, for example the conversion of propene into ethene and 2-butene, and cross- or co-metathesis, which is taken to mean the reaction of two different olefin types, for example the reaction of propene and 1-butene to give ethene and 2-pentene. If one of the reaction partners is ethylene, the term ethenolysis is generally used.

Furthermore, olefin metathesis gives access to unsaturated polymers, more precisely by ring-opening metathesis polymerization (ROMP) of cyclic olefins and by acyclic diene metathesis polymerization (ADMET) of α,ω-dienes. Examples of more recent applications are the selective ring opening of cyclic olefins using acyclic olefins and ring closure reactions (RCM), by means of which unsaturated rings of different ring size can be prepared, preferably with α,ω-dienes being used. Suitable catalysts for metathesis reactions are a multiplicity of transition-metal compounds, in particular those from sub-groups VI to VIII of the Periodic Table of the Elements. The catalysts used may be homogeneous or heterogeneous.

In general, heterogeneous olefin metathesis catalysts are used in industrial applications. These are based, in particular, on rhenium, molybdenum and tungsten oxides, which are generally immobilized on oxidic supports, for example $SiO_2$, $Al_2O_3$, $SiO_2/Al_2O_3$, $B_2O_3/Al_2O_3/SiO_2$, $Nb_2O_5$ or $TiO_2$.

These catalysts are in most cases prepared by means of aqueous impregnation methods, with the active compounds comprising salts, for example $NH_4ReO_4$, $HReO_4$, $NH_4WO_3$ or $NH_4MoO_3$, being immobilized on the support. However, it is also possible to work in non-aqueous solution, using, for example, $MeReO_3$ as precursor of the active catalyst species. On use of this reagent, no reaction is observed between the methyl group and the surface function of the heterogeneous support.

All the catalysts described above are distinguished by high activity and the ability to be regenerated in reactions of sterically undemanding or unfunctionalized olefins; however, on use of such functionalized olefins, for example methyl oleate, or of sterically hindered olefins with bulky substituents and/or complete substitution of the double bond, they have to be pretreated with an alkylating agent in order to increase the activity. Frequently used alkylating agents are tetramethyllead and tetramethyltin. The use of olefins containing protic functional groups, such as —OH, —$CO_2H$ or —$NHR_2$, in the metathesis reaction in which a catalyst activated in this way is employed, results in spontaneous deactivation of the heterogeneous catalyst, restricting the area of application of these catalysts.

Furthermore, only a few percent of the supported transition metal in these activated systems is catalytically active, and a multiplicity of different species exist on the surface. The desired uniform distribution of the metal compound or active species employed on the support surface is not achieved using the customary methods for the preparation of the catalysts. In particular, catalysts prepared on an industrial scale frequently do not achieve the desired activity.

Angew. Chem. Intl. Ed. Engl. 28 (1989), pp. 62–64, discloses a metathesis catalyst prepared by the immobilization of $[Cl_3W(=CHCMe_3)]$, $[(Me_3CCH_2)_3W(=CHCMe_3)]$ or $[(Me_3CO)_3W(=CHCMe_3)]$ on silica gel which has free hydroxyl groups. It is assumed that during the immobilization reaction, an oxygen-metal bond is formed which immobilizes the metal on the support.

Jean Marie Basset et al. in J. Chem. Soc. Dalton Trans 1994, pp. 1723–1729, describe the immobilization of $[W(\equiv CCMe_3)(CH_2CMe_3)_3]$ and $[W(\equiv CCMe_3)Cl_3(dimethoxyethane)]$ on $SiO_2$, $Al_2O_3$, $SiO_2/Al_2O_3$ and $Nb_2O_5$. It is assumed that a carbene unit is formed by protonation of the carbyne unit, and the remaining free valence of the metal forms a bond to the oxygen atom of the support, immobilizing the complex on the metal. The immobilized complexes are active as metathesis catalysts.

Although the catalyst systems disclosed in the above-mentioned references have a certain activity in the metathesis of olefins, this activity is, however, relatively low and in no way suitable for use on a large industrial scale.

It is an object of the present invention to provide a catalyst system which is suitable for olefin metathesis and which is, in particular, also suitable for use of relatively inert functionalized olefins without the need to carry out prior activation. Furthermore, the catalyst should as far as possible not deactivate spontaneously on contact with reactive functional groups on the olefins employed.

We have found that this object is achieved by a heterogeneous catalyst immobilized on an inorganic support, comprising at least one active rhenium compound containing at least one carbene group and, if desired, further functional groups, wherein the rhenium compound is bonded to the material used as support by a chemical bond, preferably a covalent bond.

The above-mentioned catalyst systems have high activity and thus enable the use of relatively inert, sterically hindered and/or functionalized olefins in the metathesis reaction. In addition, the metathesis reaction can frequently be carried out at low temperatures, for example room temperature. For the preparation of the active catalyst species, a precursor complex of the active species is reacted with the support, with immobilization being achieved by a chemical reaction with formation of a bond. The bond is preferably a covalent bond.

In order to ensure this immobilization, a precursor compound of the active species is, in accordance with the invention, reacted with the support. The precursor compounds have one or more reactive groups which are capable of reacting with potential groups present on the support. In this reaction between the two reactive groups, a covalent bond is formed between the support and the metal. This can occur, for example, through one or two of the groups reacting with one another being cleaved off.

The rhenium complexes used in accordance with the invention as precursor compound and as active species are in the oxidation states III to VII, preferably IV to VII, in particular V to VII.

The active complex must contain at least one carbene unit so that the activity in the metathesis reaction is ensured. This carbene unit can be introduced into the active complex through various measures. Firstly, the carbene unit may already be present in the precursor compound. It is also possible for the precursor compound to carry a precursor unit of the carbene function, from which the latter is formed during the reaction with the support. For example, a carbyne function present on the precursor compound can be converted into a carbene function by protonation by a proton present, for example, on the support. Furthermore, the precursor compound may also carry functional groups which, after immobilization of the precursor on the support, can be converted into a carbene function by a suitable chemical reaction with, for example, an organometallic reagent.

The precursor compound preferably contains at least one carbene, carbyne or alkyl unit.

In particular, the precursor compounds used in accordance with the invention have the general formula (I)

$$\text{Re}(\equiv CR^1)_a(=CR^2R^3)_b(CR^4R^5R^6)_c(X)_d \tag{I}$$

In the formula (I), $R^1$ to $R^6$, independently of one another, are selected from the group consisting of hydrogen, cyclic and acyclic, linear and branched, substituted and unsubstituted $C_1$–$C_{40}$-alkyl groups, $C_2$–$C_{40}$-alkenyl and alkynyl groups, $C_5$–$C_9$-aromatic groups and silyl groups. $R^1$ to $R^6$ are preferably, independently of one another, selected from linear and branched $C_1$–$C_{10}$-alkyl groups, $C_2$–$C_{10}$-alkenyl and alkynyl groups and $C_6$–$C_7$-aromatic groups. These groups may carry halogens, ester groups or silyl groups as substituents. In particular, $R^1$ to $R^6$ are selected from the group consisting of methyl, ethyl, propyl, i-propyl, n-butyl, i-butyl, tert-butyl, cyclohexyl, phenyl, trialkylsilyl and vinyl groups. X is selected from the group consisting of hydrogen, halogens, oxo groups, imido groups, alkoxy groups and nitride groups. The indices a, b, c and d are, independently of one another, integers from 0 to 4, preferably from 0 to 2, where the values of the individual numbers depend on the stoichiometrically necessary amount.

The precursor compounds are reacted with the support, with the reaction between the reactive groups forming the immobilized, active complex. The active complex contains, as already stated, at least one carbene unit. The active complex preferably has a composition conforming to the general formula (II)

$$\text{S—Re}(\equiv CR^1)_a(=CR^2R^3)_b(CR^4R^5R^6)_c(X)_d \tag{II}$$

In this formula, S is the support, $R^1$ to $R^6$, X and a, b, c and d are as defined above under the formula (I), where again the values for a to d arise from the stoichiometry necessary. The substances of the formula (II) are derived from the substances of the formula (I) by at least one of the substituents present in (I) being cleaved off or converted into another substituent, which takes place during the reaction with the support.

In particular, the active complex employed in accordance with the present invention is the complex of the formula (III)

$$\text{S—Re}(\equiv CR^1)(=CHR^2)(CH_2R^3) \tag{III}$$

In the formula (III), $R^1$, $R^2$ and $R^3$, independently of one another, are selected from the group consisting of linear and branched $C_1$–$C_5$-alkyl groups. The best results have been obtained using a complex of the formula (III) in which $R^1$, $R^2$ and $R^3$ are a tert-butyl group.

The reactive groups which are present on the support and with which the groups located on the precursor compound are able to react can in principle be selected in accordance with their desired reactivity. Protic groups are frequently present on the support. For the case that the oxidic supports preferred for the purposes of the present invention are used, these preferably contain hydroxyl groups, which react with the precursor compound with elimination of a proton. In this case, a metal-oxygen bond is formed, through which the active complex is immobilized. The active complexes immobilized via an oxygen atom are preferred in accordance with the invention.

Examples of oxidic supports which are preferred in accordance with the invention include $SiO_2$, $Al_2O_3$, $SiO_2/Al_2O_3$, $B_2O_3/Al_2O_3$, $B_2O_3Al_2O_3/SiO_2$, $NbO_2$, $Ti_2$, $ZrO_2$ and zeolites and clays of natural and synthetic origin. The supports may be modified by, for example, Lewis or Bronsted acids, such as sulfate ions, $BF_3$ or organoboron species. Preference is given to $SiO_2$, which may be porous or nonporous, for example mesoporous having pores of from 20 to 200 Å. In addition to the treatment with, for example, acids, the supports may also have been treated in another suitable manner, for example by heat treatment in order to remove water. In the case of the use of $SiO_2$, this may have been treated at temperatures of from 200 to 800° C. The heat treatments can be carried out under an inert-gas atmosphere or alternatively under an oxygen atmosphere.

The catalysts of the formula (II) used in accordance with the invention are, in one embodiment of the present invention, prepared by reaction of the precursor compound of the formula (I) with the support, which contains at least one suitable reactive group, resulting in the formation of the immobilized active complex.

The reaction can be carried out in a suitable inert solvent in which the precursor compound is dispersed or dissolved and then reacted with the support. Examples of suitable solvents or dispersion media are paraffins, for example pentane, hexane or cyclohexane, and ethers.

The reaction can also be carried out by vapor-coating the support with a precursor compound introduced into the gas phase, for example by sublimation.

In a further embodiment of the present invention, the active complex is prepared by reacting a compound containing reactive groups which are able to react with the reactive groups on the support with the latter. Besides the reactive group, this compound contains no organic functions. In general, the compounds of this type contain no organic substituents, such as carbyne, carbene or alkyl functions, but possibly contain alkoxy, oxo, amido, imido, nitride and/or halogen atoms, suitably also alkyl groups.

After immobilization on the support, the compound is then converted into the active complex, for example by alkylation reagents, such as organoaluminum, organozinc and Grignard compounds, alkylidene group precursor compounds, such as, for example, phosphoranes and diazoalkanes, reactive and/or unsaturated hydrocarbons, such as, for example, cyclopropane, cyclopropene, alkynes, dienes and alkenes.

The catalysts according to the invention are extremely reactive. In principle, they can be employed for all olefins whether they are reactive or inert or, if desired, contain further functional groups.

These olefins can carry terminal or internal double bonds and can be cyclic or acyclic, linear or branched. The total number of carbon atoms can be from 1 to 100, preferably from 1 to 40; the double bonds may be unsubstituted or mono-, bi-, tri- or tetrasubstituted. Furthermore, the olefins which can be employed can also be cyclic olefins, for example cycloalkenes or cycloalkadienes. Further functional groups may be present, for example further double or even triple bonds. Examples of further possible substituents are aromatic functions, ester, aldehyde, keto, nitrile, amide, alcohol and amine functions, and sulfur and phosphorus units.

The catalysts used in accordance with the invention are furthermore suitable for use, in principle, in all metathesis reactions, i.e. in self-metathesis and in the co-metathesis of acyclic olefins, such as, of course, also ethanolysis. They can furthermore be employed in the metathesis reactions explained above which are known under the abbreviations ROMP, ADMET and RCM.

During performance of the metathesis reaction according to the invention, the olefin/catalyst ratio has values of from 1 to 10,000,000, preferably from 2 to 100,000, particularly preferably from 4 to 1000.

The reaction temperature is set to values of from −50 to 400° C., preferably from 0 to 150° C., in particular from 15 to 100° C.

The reaction can be carried out in the absence of a solvent or in the presence of a solvent. If a solvent is used, this is preferably aprotic and apolar. Examples include paraffins, preferably hexane and pentane, halogenated compounds, preferably dichloromethane and dichlorobenzene, and aromatic compounds, preferably toluene. The solvent may have been degassed before the reaction. On use of a solvent, the concentration of olefins is at values of from 0.001 mol/l to 10 mol/l, preferably from 0.01 to 5 mol/l, in particular from 0.1 to 2 mol/l.

The reaction can be carried out continuously or batchwise.

When the reaction is complete, the resultant mixture is worked up by conventional methods.

The invention is now explained in the following examples:

EXAMPLES

Example 1

Preparation of Re($\equiv$CtBu)(=CHtBu)(CH$_2$tBu) on SiO$_2$

A 1.00 g of SiO$_{2\text{-}(700)}$ (0.23–0.26 mmol of surface hydroxyl groups, prepared by drying Degussa Altosil 200 m$^2$/g at 700° C. and 10$^{-5}$ mMHg) and 0.20 g of Re($\equiv$CtBu)(=CHtBu)(CH$_2$tBu)$_2$ are stirred for 2 hours at 20° C. in pentane, during which 0.24 mmol of neopentane is liberated and the support becomes a yellow color. The suspension is filtered, washed with pentane and dried at 25° C. under reduced pressure.

Analysis: 4.75% Re, 4.55% C.

B An excess of Re($\equiv$CtBu)(=CHtBu)(CH$_2$tBu)$_2$ is sublimed onto 1.00 g of SiO$_{2\text{-}(700)}$ (0.23–0.26 mmol of surface hydroxyl groups), during which the support becomes a yellow color. The support is freed from excess Re($\equiv$CtBu)(=CHtBu)(CH$_2$tBu)$_2$ under reduced pressure.

Analysis: 4.75% Re, 4.55% C.

Example 2

Reaction of 3-heptene 0.6 ml of 3-heptene in 3.0 ml of dichlorobenzene is added to 4.3 μmol of Re($\equiv$CtBu)(=CHtBu)(CH$_2$tBu) on SiO$_2$, and the mixture is stirred at 25° C. for 500 minutes. The GC analysis gives the following values (Table 1)

TABLE 1

| Time | Conversion (%) | E/Z (hex-3-ene) | E/Z (oct-4-ene) |
|---|---|---|---|
| 5 | 18.4 | 0.80 | 0.64 |
| 15 | 24.8 | 0.81 | 0.63 |
| 30 | 30.2 | 0.76 | 0.58 |
| 60 | 36.2 | 0.72 | 0.56 |
| 420 | 48.8 | 1.36 | 0.83 |
| 1140 | 49.5 | 7.01 | 4.08 |

Example 3

Reaction of Methyl Oleate 0.128 g of methyl oleate in 3.5 ml of dichlorobenzene is added to 4.3 μl of Re($\equiv$CtBu)(=CHtBu)(CH$_2$tBu) on SiO$_2$, and the mixture is stirred at 25° C. for 300 minutes. GC analysis shows a conversion of 50%.

Example 4

Reaction of Propene 8.34 μmol of Re($\equiv$CtBu)(=CHtBu)(CH$_2$tBu) on SiO$_2$ is reacted with 4.20 mmol of propene at 0.4 bar in a batch reactor (0.26 l) at 25° C. The GC analysis gives the wing values (Table 2)

TABLE 2

| Time | Conversion (%) | E/Z (but-2-ene) |
|---|---|---|
| 5 | 14.3 | 2.55 |
| 13 | 20.0 | 2.62 |
| 30 | 27.3 | 2.79 |
| 52 | 33.9 | 2.94 |

Example 5

Reaction of Propene with Isobutene 20.4 μmol of Re($\equiv$CtBu)(=CHtBu)(CH$_2$tBu) on SiO$_2$ are reacted with 5.12 mmol of propene and 5.12 mmol of isobutene at 0.66 bar in a batch reactor (0.38 l) at 25° C. GC analysis shows an isobutene conversion of 6% after 20 minutes.

Example 6

Reaction of pent-2-ene nitrile 40 mg of Re($\equiv$CtBu)(=CHtBu)(CH$_2$tBu) are introduced into a sealed reactor under argon. With vigorous stirring, 3.4 ml of 1,2-dichlorobenzene and 0.10 ml (1.032·10$^{-3}$ mol, 100 equivalents) of pent-3-ene nitrile are added successively. The reaction is carried out at 25° C. with vigorous stirring. Analysis of the reaction mixture shows that a reaction has taken place.

Example 7

Ring Closure Metathesis (RCM) of (−)-β-citronellene 40 mg of Re($\equiv$CtBu)(=CHtBu)(CH$_2$tBu) are introduced into a sealed reactor under argon. With vigorous stirring, heptane as internal standard and 0.160 g (1.157·10$^{-3}$ mol) of citronellene are added successively. The reaction is carried out at 25° C. with vigorous stirring. After 5 minutes, 56% of (−)-β-citronellene have been converted into 2-methylcyclopentene and isobutene.

We claim:

1. A heterogeneous catalyst immobilized on an inorganic support, comprising at least one active rhenium containing at least one carbene group, wherein the rhenium is bonded to the material used as support by a covalent bond, and which conforms to the general formula (II)

Support —Re(CR$^1$)$_a$(=CR$^2$R$^3$)$_b$(CR$^4$R$^5$R$^6$)$_c$(X)$_d$  (II)

in which R$^1$ to R$^6$, independently of one another, are selected from the group consisting of hydrogen, cyclic and acyclic, linear and branched, substituted and unsubstituted C$_1$–C$_{40}$-alkyl groups, C$_2$–C$_{40}$-alkenyl and alkynyl groups, C$_5$–C$_9$-aromatic groups and silyl groups, X is selected from the group consisting of hydrogen, halogens, oxo groups, imido groups, alkoxy groups and nitride groups, and the indices a, c and d, independently of one another, are integers from 0 to 4, b is an integer of 1 to 4, where the values of the individual numbers depend on the stoichiometrically necessary amounts.

2. A catalyst as claimed in claim 1, wherein the support is selected from the group consisting of SiO$_2$, Al$_2$O$_3$, SiO$_2$/Al$_2$O$_3$, B$_2$O$_3$/Al$_2$O$_3$, B$_2$O$_3$/Al$_2$O$_3$/SiO$_2$, NbO$_2$, TiO$_2$, ZrO$_2$ and zeolites and clays of natural and synthetic origin which may have been modified by Lewis or Bronsted acids.

3. A catalyst as claimed in claim 2, wherein the support is selected from clays and zeolites which have been modified by sulfate ions, BF$_3$ or organoboron species.

4. A catalyst as claimed in claim 2, wherein the support is SiO$_2$ which may be porous or nonporous.

5. A catalyst as claimed in claim 1, wherein the active rhenium compound is covalently bonded to an oxygen atom present in the support.

6. A catalyst as claimed in one of claim 1, which conforms to the formula (III)

Support —Re(CR$^1$)(=CHR$^2$)(CH$_2$R$^3$)  (III)

in which the support is a suitable support, and R$^1$, R$^2$ and R$^3$, independently of one another, are a linear or branched C$_1$–C$_5$-alkyl group.

7. A catalyst as claimed in claim 6, wherein the support is SiO$_2$.

8. A process for the preparation of a catalyst containing a rhenium compound with at least one carbene group as claimed in claim 1, which comprises contacting and reacting a suitable precursor compound of the active rhenium compound with an inorganic support, where the precursor compounds and the support each contain at least one reactive group which react with one another to form a covalent bond between the support and the rhenium, and introducing, if appropriate, a carbene function into the compound thus obtained, and wherein the precursor compound conforms to the general formula (I)

Re(CR$^1$)$_a$(=CR$^2$R$^3$)$_b$(CR$^4$R$^5$R$^6$)$_c$(X)$_d$  (I)

in which R$^1$ to R$^6$, independently of one another, are selected from the group consisting of hydrogen, cyclic and acyclic, linear and branched, substituted and unsubstituted C$_1$–C$_{40}$-alkyl groups, C$_2$–C$_{40}$-alkenyl and alkynyl groups, C$_5$–C$_9$-aromatic groups and silyl groups, X is selected from the group consisting of hydrogen, halogens, oxo groups, imido groups, alkoxy groups and nitride groups, and the indices a, c and d, independently of one another, are integers from 0 to 4, b is an integer of 1 to 4, where the values of the individual numbers depend on the stoichiometrically necessary amounts.

9. A process as claimed in claim 8, wherein the precursor compound contains at least one carbene group or at least one precursor function of a carbene group from which the latter is formed during the reaction with the support.

10. A process as claimed in claim 8, wherein the precursor compound contains at least one carbene, carbyne or alkyl unit.

11. A process as claimed in claim 8, wherein the precursor compound contains a precursor function of a carbene group, this precursor function being converted into a carbene function using a suitable reagent after the reaction between the precursor compound and the support.

12. A process as claimed in claim 8, wherein the support is selected from the group consisting of SiO$_2$, Al$_2$O$_3$, SiO$_2$/Al$_2$O$_3$, B$_2$O$_3$/Al$_2$O$_3$, B$_2$O$_3$/Al$_2$O$_3$/SiO$_2$, NbO$_2$, TiO$_2$, ZrO$_2$ and zeolites and clays of natural and synthetic origin, which may have been modified by Lewis or Bronsted acids.

13. The process as claimed in claim 12, wherein the support is selected from clays and zeolites which have been modified by sulfate ions, BF$_3$ or organoboron species.

14. A process as claimed in claim 12, wherein the support is SiO$_2$ which may be porous or nonporous.

15. A method comprising contacting an olefin in a metathesis reaction with the catalyst as claimed in claim 1.

16. The method as claimed in claim 15, wherein the metathesis reaction is carried out using olefins which are selected from the group consisting of acyclic and cyclic, terminal and internal, linear and branched, unsubstituted and mono-, di-, tri- and tetrasubstituted olefins, and where the substituents may be selected from the group consisting of double and triple bonds, aromatic functions, ester, aldehyde, keto, nitrile, amide, alcohol and amine functions, and sulfur and phosphorus units.

17. The method as claimed in claim 15, wherein the olefin metathesis is selected from the group consisting of self-metathesis, cross-metathesis, ethanolysis, and the metathesis reactions known under the abbreviations ROMP, RCM and ADMET.

18. The method as claimed in claim 15, wherein the olefin metathesis is carried out at temperatures of from −50 to 400° C., and the olefin/catalyst molar ratio has values of from 1 to 10,000,000.

19. The method as claimed in claim 18, wherein the temperature is from 0 to 150° C.

20. The method as claimed in claim 18, wherein the temperature is from 15 to 100° C.

21. The method as claimed in claim 18, wherein the molar ratio has values from 2 to 100,000.

22. The method as claimed in claim 18, wherein the molar ratio has values from 4 to 1000.

23. A catalyst as claimed in claim 1, wherein the covalent bond is other than oxygen.

24. A catalyst as claimed in claim 1, wherein X is selected from the group consisting of hydrogen, halogens, imido groups, alkoxy groups and nitride groups.

25. The catalyst as claimed in claim 1, wherein R$^1$ to R$^6$, independently of one another, are selected from the group consisting of linear and branched C$_1$–C$_{10}$-alkyl groups, C$_2$–C$_{10}$-alkenyl and alkynyl groups and C$_6$–C$_7$-aromatic groups, which may carry halogens, ester groups or silyl groups as substituents.

26. The catalyst as claimed in claim 25, wherein R$^1$ to R$^6$, independently of one another, are selected from the group consisting of methyl, ethyl, propyl, i-propyl, n-butyl, i-butyl, tert-butyl, cyclohexyl, phenyl, trialkylsilyl and vinyl groups.

27. The catalyst as claimed in claim 1, wherein the indices a, c and d, independently of one another, are integers from 0 to 2.

28. The catalyst as claimed in claim 6, wherein R$^1$, R$^2$ and R$^3$ are tert-butyl.

29. The process as claimed in claim 8, wherein R$^1$ to R$^6$, independently of one another, are selected from the group consisting of linear and branched C$_1$–C$_{10}$-alkyl groups, C$_2$–C$_{10}$-alkenyl and alkynyl groups and C$_6$–C$_7$-aromatic groups, which may carry halogens, ester groups or silyl groups as substituents.

30. The process claimed in claim 29, wherein $R^1$ to $R^6$, independently of one another, are selected from the group consisting of methyl, ethyl, propyl, i-propyl, n-butyl, i-butyl, tert-butyl, cyclohexyl, phenyl, trialkylsilyl and vinyl groups.

31. The process as claimed in claim 8, wherein the indices a, c and d, independently of one another, are integers from 0 to 2.

32. The catalyst as claimed in claim 7, wherein $R^1$, $R^2$ and $R^3$ are tert-butyl.

* * * * *